(12) United States Patent
Charron et al.

(10) Patent No.: US 10,501,765 B2
(45) Date of Patent: Dec. 10, 2019

(54) HIGH-SOLIDS BIOMASS SLURRY GENERATION FOR ENHANCED EFFICIENCY HYDROLYSIS PROCESSING AND EQUIPMENT DESIGN TO YIELD THE SAME

(71) Applicant: EDENIQ, INC., Visalia, CA (US)

(72) Inventors: Jeffrey R. Charron, Visalia, CA (US); Thomas P. Griffin, Visalia, CA (US)

(73) Assignee: Edeniq, Inc., Visalia, CA (US)

( * ) Notice: Subject to any disclaimer, the term of this patent is extended or adjusted under 35 U.S.C. 154(b) by 0 days.

(21) Appl. No.: 15/560,415

(22) PCT Filed: Mar. 25, 2016

(86) PCT No.: PCT/US2016/024344
§ 371 (c)(1),
(2) Date: Sep. 21, 2017

(87) PCT Pub. No.: WO2016/160616
PCT Pub. Date: Oct. 6, 2016

(65) Prior Publication Data
US 2018/0066293 A1    Mar. 8, 2018

Related U.S. Application Data

(60) Provisional application No. 62/139,554, filed on Mar. 27, 2015.

(51) Int. Cl.
| | | |
|---|---|---|
| *C12P 19/02* | (2006.01) | |
| *C08L 97/02* | (2006.01) | |
| *C08H 8/00* | (2010.01) | |
| *B01F 5/20* | (2006.01) | |
| *B01F 7/00* | (2006.01) | |
| *B01F 7/18* | (2006.01) | |
| *B01F 15/02* | (2006.01) | |
| *B01F 3/12* | (2006.01) | |
| *B02C 23/18* | (2006.01) | |
| *C12P 19/14* | (2006.01) | |
| *B01F 13/10* | (2006.01) | |

(52) U.S. Cl.
CPC ............ *C12P 19/02* (2013.01); *B01F 3/1221* (2013.01); *B01F 5/205* (2013.01); *B01F 7/00633* (2013.01); *B01F 7/00641* (2013.01); *B01F 7/00758* (2013.01); *B01F 7/00908* (2013.01); *B01F 7/18* (2013.01); *B01F 15/0283* (2013.01); *B02C 23/18* (2013.01); *C08H 8/00* (2013.01); *C08L 97/02* (2013.01); *C12P 19/14* (2013.01); *B01F 2003/1257* (2013.01); *B01F 2013/108* (2013.01); *C12P 2201/00* (2013.01)

(58) Field of Classification Search
CPC ..... B01F 3/1221; B01F 5/205; B01F 7/00633
See application file for complete search history.

(56) References Cited

U.S. PATENT DOCUMENTS

| | | |
|---|---|---|
| 5,498,766 A | 3/1996 | Stuart et al. |
| 7,807,419 B2 | 10/2010 | Hennessey et al. |
| 8,420,356 B2 * | 4/2013 | Medoff ................. C12M 21/12 435/105 |
| 2013/0210085 A1 | 8/2013 | Kilner et al. |

OTHER PUBLICATIONS

International Search Report and Written Opinion dated Jun. 23, 2016 in PCT/US2016/024344, filed Mar. 25, 2016, 11 pages.
Grundfos Industry, Pump Handbook, Grundfos Management A/S, Bjerringbro, Denmark, 2004, 145 pages.

* cited by examiner

*Primary Examiner* — Pancham Bakshi
(74) *Attorney, Agent, or Firm* — Kilpatrick Townsend & Stockton LLP (57) ABSTRACT

This disclosure provides a high solids biomass slurry that is readily pumpable and transportable to downstream processing units, such as chemical and/or biochemical processing units. The slurry is amenable to saccharification efficiencies of >70 % in processing times of <36 hours. Also provided are devices for processing materials, such as the high solids biomass slurry.

10 Claims, 9 Drawing Sheets

HIGH-SOLIDS BIOMASS SLURRY GENERATION FOR ENHANCED EFFICIENCY HYDROLYSIS PROCESSING AND EQUIPMENT DESIGN TO YIELD THE SAME

CROSS-REFERENCE TO RELATED PATENT APPLICATIONS

This application claims the benefit of priority to U.S. Provisional Application No. 62/139,554, filed Mar. 27, 2015, which is incorporated by reference herein in its entirety.

BACKGROUND OF TINE INVENTION

The processing of biomass and biomass-derived materials is often undertaken with the objective of chemical or biochemical processing to yield fuels and or chemicals (often referred to as "biofuels" or "biochemicals"). Initial processing steps toward this objective typically include hydration and hydrolysis to yield sugars or sugars-rich intermediates; this transformation is also referred to as "saccharification".

Material and energy efficiencies of the hydration and hydrolysis steps are often largely determined by the preprocessing and pretreatment of the biomass material, which typically begins in its solid-phase physical state. These efficiencies are directly impacted by solid particle size and size distributions, effectiveness of dispersion of the solid mass in concert with its mixing and wetting with added water ("hydration"), and the degree to which this two-phase mixture can be homogenized and transported in this state to downstream unit operations. In addition, it is usually advantageous—provided the above conditions can be maintained—to maximize the practically achievable solids content in the resultant two-phase slurry mixture. This attribute establishes increased intensity of chemical and or biochemical reactions downstream, in turn enabling reduced capital cost in those unit operations—as well as reduced energy costs associated with subsequent product separations and water recovery.

The prior art includes a variety of dispersing and mixing devices and techniques including those defined by Medoff in U.S. Pat. No. 8,420,356 B2 and U.S. application Ser. No. 13/789,102 and U.S. Ser. No. 14/224,340 in which a lignocellulosic feedstock is saccharified or liquefied into monomeric sugars utilizing a dispersing system to dispense the fibrous feedstock in the recycle loop of a batch saccharification process at high solids loadings.

Some strategically important biomass materials—notably corn stover and sugarcane bagasse—tend to be of low density in dry transport, as well as resistant (recalcitrant) to hydration. For these materials, it is desired to achieve effective and efficient mixing with water, hydration (including thorough wetting), and high-solids homogeneous slurries. The present invention facilitates the generation of these slurries for the objectives of biofuels and or biochemical production—particularly in the application of these challenging, yet strategically important feedstock classes.

BRIEF SUMMARY OF THE INVENTION

In one aspect, the disclosure describes a high solids biomass slurry. For example, the slurry can have greater than 20% by weight bulk solid materials. Thus, in some embodiments, the slurry comprises or consists of greater than 20% by weight bulk solid materials. In some embodiments, the slurry is a homogenous, hydrated slurry. In some embodiments, the slurry is readily pumpable and transportable to downstream processing units. In some embodiments, the downstream processing unit is a chemical and/or biochemical processing unit operation. In some embodiments, the water retention value of the slurry is greater than 2.5 gm $H_2O$ per gm solids. In some embodiments, the biomass solids are derived from corn stover or sugarcane bagasse residual materials.

In some embodiments, the downstream processing is hydrolysis or saccharification. The high solids slurry described herein has the advantage of increased saccharification efficiencies compared to previous slurries. In some embodiments, the slurry is amenable to saccharification efficiencies of >70% in processing times of <36 hours. In some embodiments, the slurry is amenable to saccharification efficiencies of >70% in processing times of <24 hours.

In some embodiments, the hydrated slurry of biomass solids comprises or consists of greater than (>) 20% (by weight) solid material. For example, in some embodiments, the hydrated slurry of biomass solids comprises >25%, >30%, or >35% (by weight) solid material.

In another aspect, a device for mixing and/or homogenizing and/or dispersion processing of materials is described. For example, in some embodiments, device includes the following components:

a. One or more stages of shear cutting elements to initially process incoming solids (by shear cutting and dispersion) prior to or in tandem with water introduction;

b. a series of two or more impeller stages—positioned in between the shear cutting stages and the discharge impeller stage—to enhance mixing and homogenization;

c. a "pumping ring" to enable highest solids and pumpability at the outlet of the discharge impeller and introduction to the device discharge port.

In some embodiments, the device is used in serial tandem with a downstream milling device that is useful for reducing the particle size and further homogenizing the material to produce a pretreated material suitable for downstream enzymatic hydrolysis processing. In some embodiments, the downstream milling device is a colloidal mill. In some embodiments, the biomass material processed by the device is corn stover or sugarcane bagasse. In some embodiments, the device is a hybrid device that is capable of mixing, homogenizing, dispersing, and milling the slurry. In some embodiments, the hybrid device is constructed in a single housing.

In another aspect, a device or tandem device(s) for mixing and/or homogenizing and/or dispersing and/or milling of biomass materials is described. In some embodiments, the device generates a homogenous, hydrated slurry of biomass solids consisting of >20% (by weight) solid material that is readily pumpable and transportable to downstream chemical processing and/or biochemical processing unit operations, such as enzymatic hydrolysis. In some embodiments, the device or tandem device(s) comprises the following components:

a. One or more stages of shear cutting elements to initially process incoming solids (by shear cutting and dispersion) prior to or in tandem with water introduction;

b. a series of two or more impeller stages—positioned in between the shear cutting stages and the discharge impeller stage—to enhance mixing and homogenization;

c. a "pumping ring" to enable highest solids and pumpability at the outlet of the discharge impeller and introduction to the device discharge port;

d. one or more colloidal mills or colloidal mill stages that reduces particle size and further enhances slurry phase dispersion In some embodiments, the device or tandem device(s) produces a slurry that is amenable to saccharification efficiencies of >70% in processing times of <24 hours. In some embodiments, saccharification enzymes are introduced to the device into one or more of the shear zone, pumping zone, discharge impeller outlet or discharge port of the device(s). In some embodiments, the saccharification enzymes include one or more enzymes from the enzyme classes of cellulases, glucanases, xylanases, ligninases, or peroxidases.

Definitions

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The term "biomass" or "biomass feedstock" refers to any material comprising lignocellulosic material, whole grains, starches, inulin, or any other type of structural hydrocarbon. Lignocellulosic materials are composed of three main components: cellulose, hemicellulose, and lignin. Cellulose and hemicellulose contain carbohydrates including polysaccharides and oligosaccharides, and can be combined with additional components, such as protein and/or lipid. Examples of biomass include agricultural products and waste products such as but not limited to grains, e.g., corn, wheat and barley; sugarcane; corn stover, corn cobs, tubers, Jerusalem artichoke, stalks, and/or other inedible waste parts of food plants; food waste, grasses such as switchgrass; and forestry biomass, such as wood, paper, board and waste wood products.

The term "lignocellulosic" refers to material comprising both lignin and cellulose, and may also contain hemicellulose.

The term "cellulosic," in reference to a material or composition, refers to a material comprising cellulose, and may also contain hemicellulose.

The term "slurry" or "slurries" refers to mixtures of biomass and water in which some of the water is hydrated into the biomass fiber structures, some of the water is contained within the external pore structure of the fiber web or mat, some of the water is contained within the fine pore structures of the fibers and fibrils, and some water is contained within the cell walls. Characterization of the degree of hydration of the biomass is simplified into two groups—"intra-fiber" and "inter-fiber" water. The inter-fiber water is primarily trapped between the fibers and is sometimes considered "bulk water", externally held within the larger pores of the fiber web; "intra-fiber water" is the water contained within the fine pores of the cell wall structures and within the intracellular structures. Mechanical preprocessing and thermal preprocessing of lignocellulosic fibers increase the intra-fiber water by increasing the number of fine pores and opening and exposing intracellular fibril pore structures to the bulk water allowing them to be saturated and retain water. Retained water within the pore structures provided accessibility channels for enzyme transport and access to the target glucan and xylan polymeric chains.

The "water retention value (WRV)" is the ratio of the mass of water in a sample to the mass of dry matter in a sample of biomass. Measurement of a biomass sample's WRV is achieved by a standard laboratory separation such as centrifugation. The baseline process for measuring WRV is to equip a standard 50 ml lab centrifuge tube with a filter set (i.e., a glass microfiber filter disk sandwiched between a 60-mesh screen disk at the bottom and 200-mesh screen disk on top) upon which the measured mass of biomass is loaded. Samples containing ~1% solids were prepared for WRV determination. Free water was removed by centrifuging the samples at 900×g for 30 min, and the wet weight of the samples was measured. The samples were then dried at 105° C. for at least 3 h, and the dry weight of the samples was measured. WRV was determined by the ratio of milligrams of water retained to milligrams of dry biomass.

The term "dissolved solids" refers to sugars, soluble carbohydrates, polysaccharides, residual lignin, and other such substances that are contained in a liquid in molecular, ionized or micro-granular suspended form. Generally the operational definition is that the solids must be small enough to pass through a filter with a two micrometer or smaller pores or other solid-liquid separation methods. Exemplary solid-liquid separation methods include, but are not limited to, membrane filtration, tangential flow filtration (TFF), centrifugation, sedimentation and flotation.

The term "conditions suitable to hydrolyze components of the biomass to sugars" refers to contacting the solids phase biomass with hydrolytic enzymes including, but not limited to, cellulase, hemicellulase and auxiliary enzymes or proteins in order to produce fermentable sugars and short chain oligomers from polysaccharides in the biomass. The conditions can further include a pH that is optimal for the activity of saccharification enzymes, for example, a pH range of about 4.0 to 7.0, or a subset within that range. The conditions can further include a temperature that is optimal for the activity of saccharification enzymes, for example, a temperature range of about 35° C. to 75° C., or a subset within that range. The conditions can further include a combination of conditions with and without enzymes and/or chemicals and with or without mechanical shear and mixing, which promote the hydrolysis or partial hydrolysis of the polymeric hydrocarbons into sugars and short chain oligomers of sugars. The conditions suitable to hydrolyze components of the biomass to sugars also include any condition(s) that support the conversion of the polysaccharides in the biomass to short chain sugars, cellobiose, and monomeric sugars. Conversion can incorporate any of the various chemical and thermal chemical means available, such as hydrolysis by acids, bases, or other chemicals.

The term "saccharification" refers to production of fermentable sugars and short chain sugar oligomers from biomass or biomass feedstock. Saccharification can be accomplished by hydrolytic enzymes and/or auxiliary proteins, including, but not limited to, peroxidases, laccases, expansins and swollenins. Saccharification can also be accomplished by chemical and thermal hydrolysis without specific enzymes or at conditions. Saccharification is conducted under conditions suitable to hydrolyze components of the biomass to sugars. The term "saccharification efficiency" refers to ratio of the quantity of fermentable sugars and short chain sugar oligomers produced during saccharification to the theoretical quantity of fermentable sugars and short chain sugar oligomers contained in the biomass prior to saccharification, expressed as a percentage.

The term "fermentable sugar" refers to a sugar or short chain sugar oligomers that can be converted to ethanol or other products such as (but not limited to) butanols, propanols, succinic acid, acetic acid, and isoprene during fermentation, for example during fermentation by yeast. For example, glucose is a fermentable sugar derived from hydrolysis of cellulose, whereas xylose, arabinose, mannose and galactose are fermentable sugars derived from hydrolysis of hemicellulose.

The term "conditions suitable for fermentation" refers to conditions of temperature, pH, solids levels, enzyme concentrations, micro-organism concentrations, and other conditions which support the conversion of sugars and short chain sugar oligomers into ethanol or other products. The term "micro-organism" refers to yeast, bacteria, or a combination thereof or other organism which support the conversion of sugars into desirable products.

The term "simultaneous saccharification and fermentation" (SSF) refers to providing saccharification enzymes or other conditions suitable to hydrolyze components of the biomass to sugars during the fermentation process. This is in contrast to the term "separate hydrolysis and fermentation" (SHF) steps.

The term "pretreatment" refers to treating the biomass with physical, chemical or biological means, or any combination thereof, to render the biomass more susceptible to hydrolysis, for example, by saccharification enzymes. Pretreatment can comprise treating the biomass at elevated pressures and/or elevated temperatures. Pretreatment can further comprise physically mixing and/or milling the biomass in order to reduce the size of the biomass particles, change its pore size distribution, and disrupt the structural components or microstructure of the biomass. Devices that are useful for physical pretreatment of biomass include, e.g., hammer mills, shear mills, cavitation mills, colloid mills, ball mills, end mills, grinders, crushers, plate mills, disk mills, or other high-shear mills used to grind, cut, shear, shred, fiberize, pulverize, crack, rub, curl, fluff, twist, hill, blend, or refine the biomass. The pretreatment process can be accomplished with the biomass in the dry, moist, or wet state and at various pressures and temperatures. An exemplary colloid mill is the Cellunator™ (Edeniq, Visalia, Calif.). Reduction of particle size is described in, for example, WO2010/025171, which is incorporated by reference herein in its entirety.

The term "pretreated biomass" refers to biomass that has been subjected to pretreatment to render the biomass more susceptible to hydrolysis.

The term "elevated pressure," in the context of a pretreatment step, refers to a pressure above atmospheric pressure (e.g., 1 atm at sea level) based on the elevation, for example at least 5, 10, 15, 20, 30, 40, 50, 60, 70, 80, 90, 100, 110, 120, 130, 140, or 150 psi or greater at sea level.

The term "elevated temperature," in the context of a pretreatment step, refers to a temperature above ambient temperature, for example at least 30, 50, 80, 100, 110, 120, 130, 140, 150, 160, 170, 180, 190, or 200 degrees C. or greater. When used in thermal pretreatment (TPT), the term includes temperatures sufficient to substantially increase the pressure in a closed system. For example, the temperature in a closed system can be increased such that the pressure is at least 100 psi or greater, such as 110, 120, 130, 140, 150 psi or greater and is in phase equilibrium with the temperature of the volatile components in the mixture.

The term "hydrolysis" refers to breaking the glycosidic bonds in polysaccharides to yield simple monomeric and/or oligomeric sugars. For example, hydrolysis of cellulose produces the six carbon (C6) sugar glucose, whereas hydrolysis of hemicellulose produces the five carbon (C5) sugars xylose and arabinose. Hydrolysis can be accomplished by acid treatment or by enzymes such as (but not limited to) amylase, cellulose, β-glucosidase, xylanase, glucoamylase, inulinase, and others, as well as mixtures or cocktails including any subset of those enzyme components. Examples of hydrolytic enzymes include cellulases and hemicellulases. "Cellulose" is a generic term for a multi-enzyme mixture or cocktail including exo-cellobiohydrolases, endoglucanases and β-glucosidases which work in tandem combination to hydrolyze cellulose to cellobiose and glucose.

The term "inhibitor" refers to a compound that inhibits the saccharification and/or fermentation process. For example, both cellobiose and glucose inhibit the activity of cellulase enzymes. For example, xylo-oligomers, xylanase inhibitor proteins (XIP), and xylose inhibit the activity of hemicellulases. Other inhibitors include sugar degradation products that result from pretreatment of lignocellulose and/or cellulose. Examples of other inhibitors include 2-furoic acid, 5-hydroxy methyl furfural (HMF), furfural, 4-hydroxybenzoic acid (HBA), syringic acid, vanillin, syringaldehyde, p-coumaric acid, ferulic acid, organic acids such as acetic acid, and phenolic compounds from the breakdown of lignin. These inhibitors can also inhibit fermentation by inhibiting the activity of yeast.

DETAILED DESCRIPTION OF THE INVENTION

Introduction

Devices have been manufactured to accomplish the generation of slurries from a range of solids, and to achieve the qualitative attributes of slurry mixing and hydration, as well as solids dispersion. A primary example is the MHD-2000 product offered by IKA Works (Wilmington, N.C.). Novel and non-obvious improvements to this existing art have been developed in the present application to further enable these devices to process low-density, hydration resistant (i.e., recalcitrant) solids, enable solids loadings at levels greater than those previously achieved, and thus facilitate capital- and energy-efficient downstream hydrolysis (i.e., saccharification) of these materials in the production of biofuels and/or biochemicals.

The key embodiment of the present invention is the production of the desired high-solids, homogeneous slurry that can be readily transported and further processed with high-efficiency—including saccharification, product separation, and water recovery and recycle. Specific modifications to the existing equipment art have been achieved that yield "hybrid" equipment functionality—notably including inlet solids particle shearing and size reduction, with combined attribute improvement of increased wettability and increased reactivity toward both hydration and hydrolysis. Additional improvements to the existing art improve pumpability of resultant slurries out of the mixing stage at very high solids loading levels—loading levels novel for biomass processing in these applications.

Equipment has been developed and applied for the processing of slurried solids (usually aqueous slurries) to include the functionalities of mixing, hydration, dispersion, homogenization, and milling/sizing. More specifically, for the handling of cellulosic biomass materials in high-loading processing, with the combined purposes of all of the above functionalities—and enabling high-conversion, low-residence time downstream hydrolysis reactions (e.g., enzymatic saccharification), specific mixing/hydration/dispersion and slurry homogenization and milling equipment has been customized for this application and deployed in tandem to achieve these targeted attributes. High-loading processing or high-solids slurries are biomass mixtures with greater than 10% wt solids on a dry mass basis, greater than 12% wt solids, greater than 15% wt solids, greater than 18% wt solids, greater than 20% wt solids, greater than 22% wt solids, greater than 25% wt solids, and greater than 30% wt solids.

A mixing-hydration-dispersion processor (MHD; for example, from IKA Works USA—Wilmington, N.C.) has been developed specifically for this application. One embodiment of this device 100 is conceptually shown in FIG. 1. Dry solid biomass 101 is introduced directly into the feed zone 122 or through a feed hopper assembly 103 designed to provide continuous feed to the device 100 ensuring delivery of consistent hydrated biomass 104 to downstream processes. The biomass first enters a hydration zone 123 in which process liquid 102 is introduced to mix with the biomass 101. The process liquid 102 comprises water. In some embodiments the process liquid 102 includes other components comprising buffering agents such as but not limited to Mg(OH)2, NaOH, other bases, sulfuric acid, acetic acid, HCl, other acids, and or enzymes. The wetted biomass then passes into the shear zone 124 in which the shear forces work the biomass into smaller particles and finer structures. In some embodiments the feedstock is delivered in the form of pellets and the shear zone function is to break the pellets and enhance hydration. In some embodiments the shear zone is additionally equipped with shear cutting elements that not only break the pellets and fibers but introduce a much higher degree of shear resulting in cutting and fracturing the fibers and particles. In these embodiments the shear zone 121 substantially decreases the average size of the biomass particles to the target zones of less than 1 mm in length. In all embodiments the shear forces in combination with the presents of water increases the retained water content of the biomass by opening intercellular structures and decreasing the average pore size enhancing their water adsorption and retention. The hydration zone 123 and shear zone 124 can be in close proximity to further enhance the water retention characteristic of the biomass. Water is co-introduced through the side or top nozzle, and mixes intimately with the solids in the initial shear zone such that the thermal energy generated by the shear forces is dispersed throughout the bulk mixture—mitigating localized temperature increases. Downstream the biomass enters into a centrifugal pump zone 125 that creates an outward centrifugal force to the hydrated biomass and delivers the hydrated biomass to the outside diameter of the chamber or the discharge impeller zone 126. This zone is equipped with a sweeping bar impeller that moves the biomass around the exterior wall and transfers the wet biomass to the outlets slurry port 127.

Figure 2A:
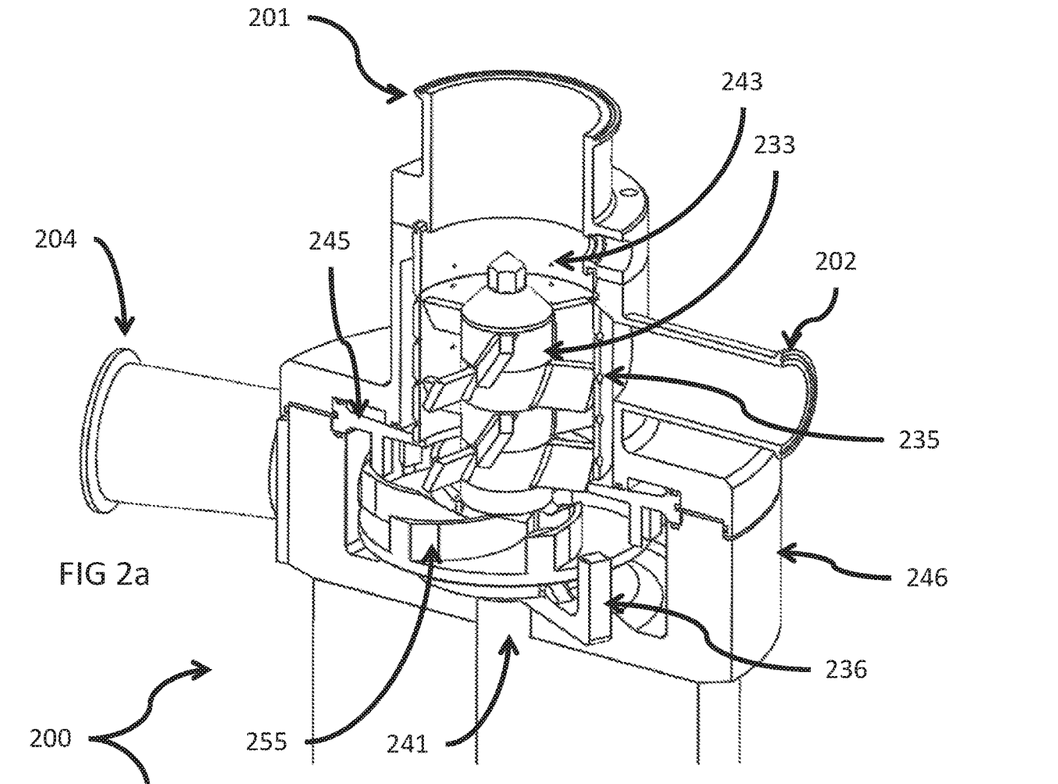
FIGS. 2A and 2B illustrates a specific configuration of the inventive device and assemblies associated with the apparatus.
Figure 2B:
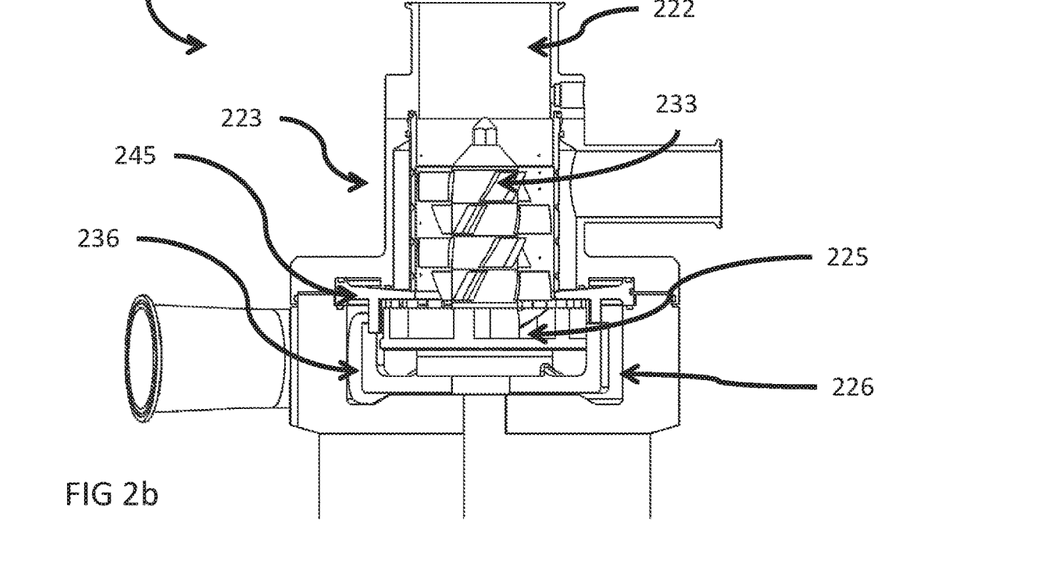

Alternative embodiments of the device 200 are illustrated in FIGS. 2a and 2b, which illustrates one configuration most useful when the feed stock is pelletized and has a bulk density of greater than 0.5 kg per liter, or greater than 0.75 kg/lit, or greater than 1.0 kg/lit. In this embodiment the inlet port 201 is maximized to minimize the feed restriction as biomass enters the feed zone 222, and the exit port 204 is configured tangentially to the device's diameter to enhance the delivery pressure of the hydrated biomass. The assembly is designed with an external housing assembly and internal rotating shaft with various components to enhance the mixing, hydration and dispersion of the biomass and the liquid or water. The inlet liquid port 202 is configured to deliver water to the hydration zone 223, which is equipped with a distribution wall 235 that has a pattern of holes 243 designed to allow a uniform spray of liquid into the hydration zone as the biomass flows downward. The hydration zone 223 is equipped with a paddle mixing bars 233 which can be equipped with paddles designed to force the biomass outward toward the hydration wall and downward toward the centrifugal pump zone 225. At the lower region of the hydration zone an isolation disk 245 is used to isolate the centrifugal zone 225 and minimize internal recirculation patterns within the zone. Hydrated biomass enters the centrifugal impeller 255 which forces the material outward toward the discharge impeller zone 226. In some embodiments the flow path between the centrifugal impeller 255 and the discharge impeller 236 is equipped with a stationary wall barrier or stator consisting of segmented teeth with 60%, 50%, 40%, or 30% of the flow path blocked to create another high shear zone as the biomass material is expelled from the device. This stator can be integrated with the isolation disk 245. Rotating with the assembly is a discharge impeller 236 that is part of the shaft 241 assembly. This impeller 236 sweeps all of the hydrated biomass from the zone 226 and around the inside diameter of the housing 246 and toward the tangential exit port 204. The discharge impeller 236 and the tangential exit port 204 provide advantages not found in prior devices.

The paddle mixing bars 233, centrifugal impeller 255 and the discharge impeller 236 are all assembled on the rotating shaft 241 providing a direct drive constant speed of rotation for all components. In some embodiments these are all rotating at the same rotational speed, but in some embodiments the direct drive gear transitions are used between the shaft 241 and the component to decrease the rotational speed of a specific component. For example the discharge impeller 236 can be geared to rotate at 50% or 75% or 85% or 95% of the speed of the centrifugal impeller to enhance the compression of the hydrated biomass against the wall before it is sweeps around to the outlet port 204. This feature helps to compress the biomass of entrained air and to generate denser slurry of biomass delivered from the device. This embodiment also enhances the compositional characteristic of the hydrated biomass which can be important for downstream operations such as but not limited to wet milling with the Cellunator or other rotor stator type mills such as colloidal mills and others including typical paper making process mills such as plate type mills. The direct drive gear transition can be implemented to reverse the rotational direction of the discharge impeller 236 with respect to the centrifugal pump impeller and change the movement of material out of the device.

Alternative embodiments of the device 200 can include auger feed mechanisms assembled to the drive shaft 241 and located in the center of the feed zone 222 above the paddle mixing bars 233 to enhance the reliable movement of biomass into the hydration zone 223. All of these alternative configurations are enhanced by the inclusion of the discharge impeller 236 and the tangential flow exit 204. In some embodiments of the device 200 the isolation plate 245 is equipped with a vertically downward facing fingers or interrupted stator wall (as shown) that is positioned between the centrifugal pump impeller 255 and the sweep bar 236 creating additional shear force on the biomass for particle size reduction and mixing and hydration.

The hydration zone 223 can be configured to include additional stages and mixing vanes that further mix the solids and water, enabling hydration, while providing centrifugal driving force for solids dispersion and slurry homogenization. After two or more stages of mixing blades in series, the slurry reaches the discharge sections or the centrifugal pumping zone 225 and discharge impeller zone 226 from which it is pumped out of the unit. The inclusion of the discharge wipers or pumping rings help clear the solids and slurry from the zone, and direct concentrated slurry flow into the discharge port 204. The discharge impeller can consist of any number of configurations including a sweep bar assembly with 2, 3, 4, or more vertical bars to sweep the solids off the inside circumference of the housing 246. Alternative embodiments include two rotating bar assemblies, one that sweeps the hydrated biomass off the outside diameter of the centrifugal impeller 255 and one that sweeps the solids off the inside diameter of the housing 246. As described previously, the rotational speed and direction of these multiple sweeping discharge impeller 236 can be the same or different from the rotational characteristics of the centrifugal impeller 255.

Figure 1:
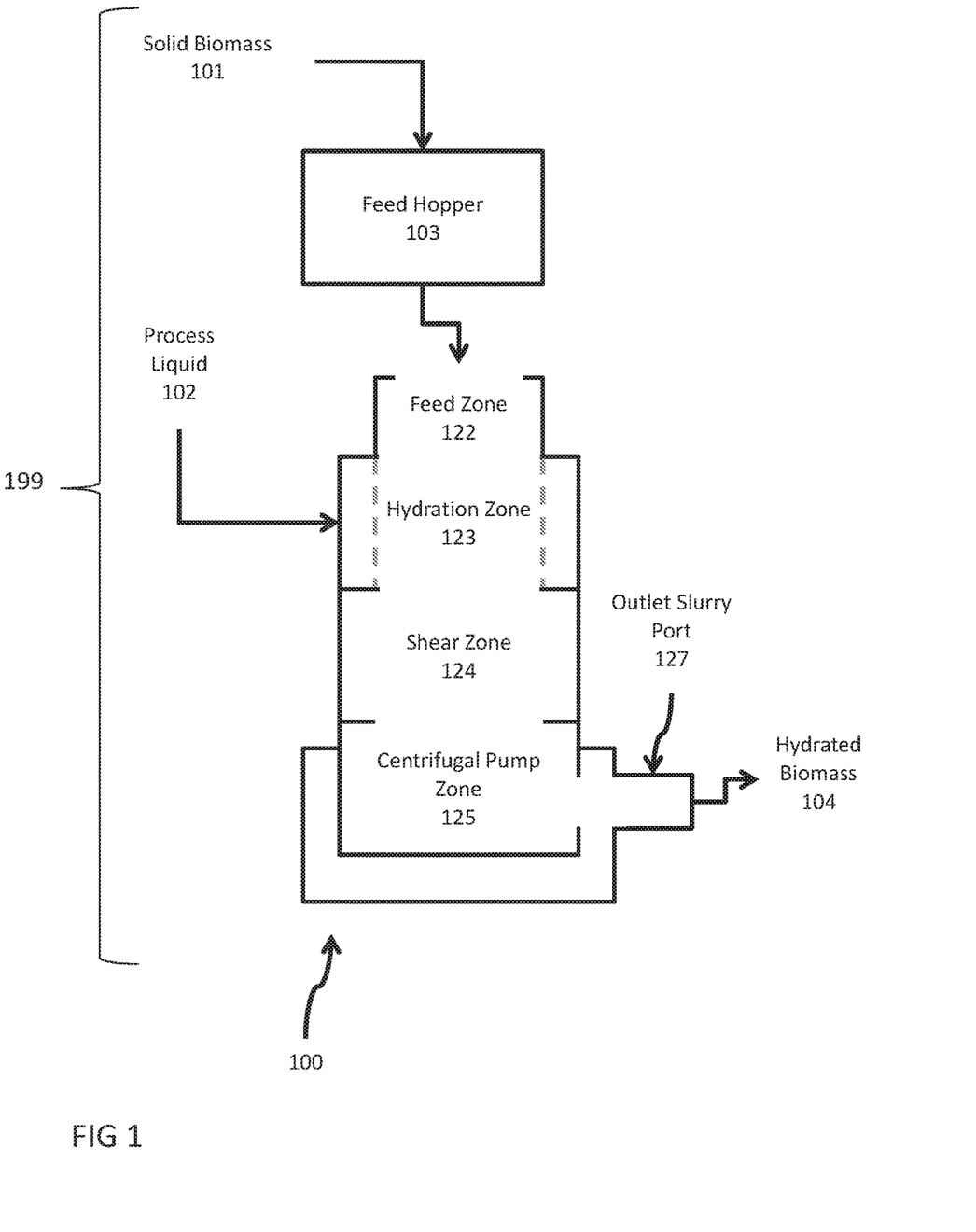
FIG. 1 illustrates a conceptual configuration of the inventive hardware for continuous biomass processing prior to saccharification.

Depending on the feedstock and the form of the feedstock, such as pellets, long fibers, medium fibers, or fine fibers, the specific configuration the device 100 or 200 may vary for optimum performance and biomass mixing, hydration, and dispersion. In some embodiments the feed zone 122 or 222 is equipped with rotating auger elements that help transport the biomass from the feed zone 122 or 222 into the hydration zones 123 or 224. In the case of pellets this auger element is useful, but in the case of loose, longer fibers the auger element is less effective.

In some embodiments of the device and the process configuration a slurry milling device, such as a colloid mill, can be installed in series with the mixing, hydration and dispersion device. This provides the serial functionality of hydrating the biomass followed by milling and particle size reduction, taking advantage of the highly dispersed solids in the hydrated slurry provided directly from the device. The combined effect generates a fine-particle, high-loading, homogenous biomass solids aqueous slurry. The biomass solids aqueous slurry can have optimal characteristics for downstream processing. This intermediate product is ideally suited for hydrolysis processing of very high efficiency: i.e., high-conversion, low-residence time requirement enzymatic saccharification. The slurry can have homogeneous hydration with solids levels of 10%, 15%, 20%, 25%, 30%, 35%, or greater weight percent solids. The consistency of the homogeneous hydrated solids can be maintained using this device by managing the constant solids feed rate of dry solids into the device using the feed hopper assembly 103 and managing the constant liquid feed rate into the device. Alternative biomass hydration processes such as batch mixing or semi-batch mixing of biomass into a tank with water cannot produce continuous operation with consistently controlled levels of hydration. Dried biomass can be extremely hydrophobic and initial wetting and hydration can be inconsistent with some material floating on the tank and some fibers being wetted and having a density greater than water allowing them to sink to the bottom of the tank. Even with controlled water and biomass feeds into a bulk batch hydration tank the consistency of the delivered or extracted solids can vary and fluctuate greatly. Introducing recirculation and in tank shear mixing can improve the consistency, but inconsistency of the initial, incoming hydrophobic material remains a critical issue. Even using an inline hydration device within a recirculation loop around the tank results in inconsistency of solids levels especially when the target solids are greater than 15% or greater than 20% because the solids level of the slurry in the tank has to been less than the solids level out of the device because of the fresh dry biomass being feed into the device. As higher solid levels are targeted the mixing of the recycled solids and the bulk solids in the tank become the critical control factor for the consistency of the delivered solids. This innovative hydration configuration 199 of managing dry biomass feed with the feed hopper assembly 103 into the mixing, hydration and dispersion device 100 provides a unique solution to delivering a controlled mass flow rate and degree of hydration for downstream processes.

Integrating the shear functions of the paddle mixing bars 233 into the hydration zone 223 provides additional benefits of improving the effectiveness of the hydration achieved with the device. As defined water mixed with biomass can be bulk water or retained water. Bulk water can be removed from the biomass by centrifugal forces while retained water is fully hydrated into the fiber and fibril structures of the biomass. The innovative device provides biomass hydration that enhances both the bulk water and the retained water. The latter is most important effective downstream processing such as enzymatic saccharification The device produces hydrated biomass with an increased retained water content of 5%, 6%, 7%, 8%, 9%, 10%, 11%, 12%, or greater than 13%. The device achieves the mixing, hydration, and dispersion of the biomass solids and liquid such that the hydrated biomass achieves a retained water content of greater than 55%, 56%, 57%, 58%, 59%, 60%, 61%, 62%, 63%, 64%, or greater than 65% and delivers the hydrated biomass solids with a controlled bulk solids content of greater than 15% wt solids, 20% wt solids, 25% wt solids, or greater than 30% solids. The controlled biomass solids level out of the device is continuously managed to maintain the bulk solids level within less than 20%, less than 15%, less than 10%, or less than 5% variability from minute to minute or from hour to hour on a continuous bases. The device provides an ability to produce up to 75 psi of discharge pressure or less based on downstream losses and pressure requirements. When the device is used upstream of a device such as the Cellunator, discharge pressures produced are managed between 0 and 15 psi, or 15 and 40 psi, or 40 and 65 psi. Pressure delivery is similar to that of a centrifugal pump, where solids particle size, concentration, and other properties of the liquid that make up viscosity or rheology all affect potential discharge pressure capabilities.

Figure 3A:
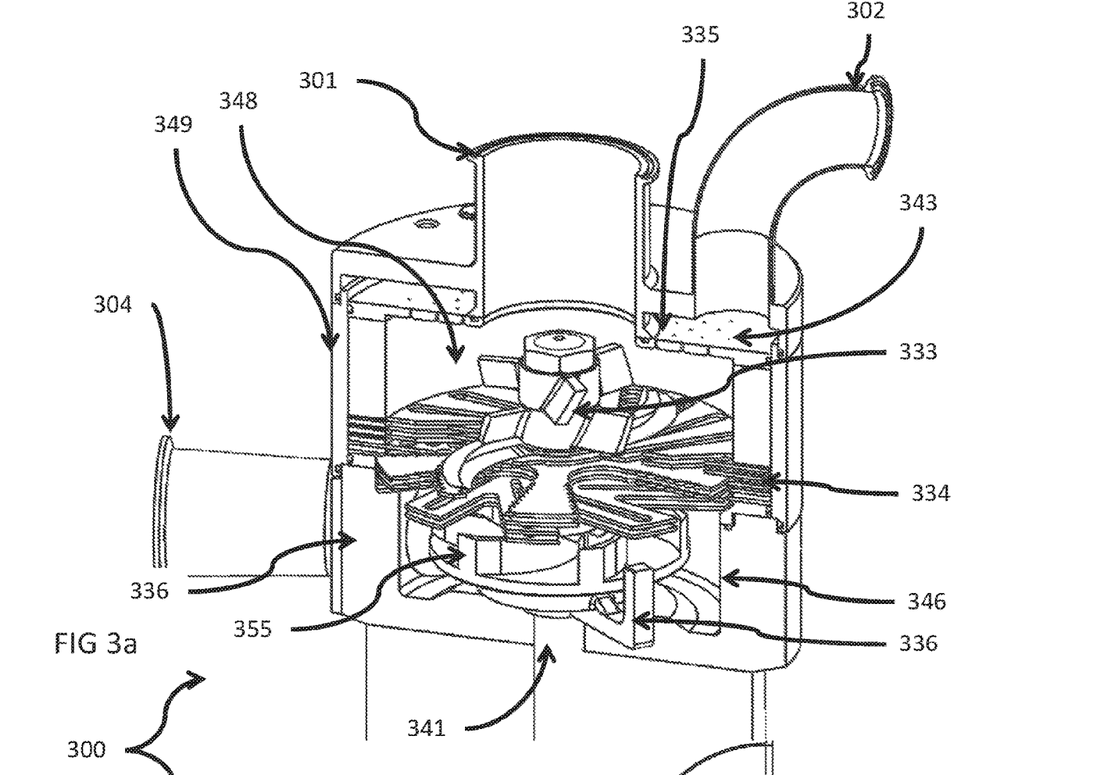
FIGS. 3A and 3B illustrates an alternative configuration of the inventive device that incorporates a high shear rotor stator section for particles size reduction in combination with mixing, hydration and dispersion.
Figure 3B:
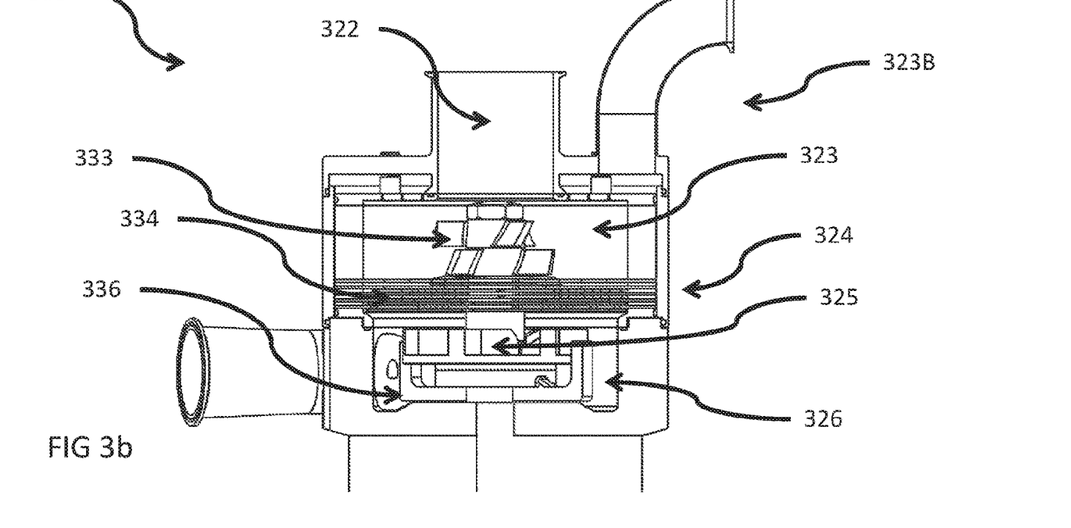

An alternative embodiment of the device is shown in FIG. 3 in which the mixing, hydration, dispersion device 300 has been modified to incorporate functionality of the particle size reduction in combination with the function of mixing, hydration and dispersion. In this embodiment the dry or as received solids (typically 50% to 95% solids) are feed thru port 301, while liquid or water is feed thru port 302 and hydrated biomass is expelled thru port 304. The biomass feed rate is controlled by the operation of the biomass feed hopper (103) and the water feed rate is controlled by a flow control value or similar device upstream of the liquid feed port 302. In this embodiment the biomass passes thru the feed zone 322 into the hydration zone 323 which in this embodiment is oriented with a down flow water feed direction. The hydration zone paddle mixing bars 333 has been decreased to two elements. If the biomass is feed as low density, loose fibers the paddle mixing bars 333 can collect the fibers as a bundle blocking the feed zone 322, and therefore, the design and number of the paddle mixing bars 333 can be tailored based on the style of feedstock being processed. The hydration zone 323 water distributions is provided by the feed plate 335 which are covered in a pattern of holes 343 to provide uniform distribution of water or liquid into the biomass passes through the hydration zone.

Illustrated in this embodiment 300 is a shear cutting and particle size reduction assembly 334 which is consistent with the shear zone 124 of FIG. 1. The shear cutting assembly 334 consists of a series of alternating rotor and stator plates which cut, grab, and impact the biomass and expose it to high shear forces as the rotor plates rotate with respect to the stationary stator plates. The biomass fibers are cut if vertically trapped between adjacent plates and can be mechanically rolled milled if horizontally trapped between adjacent plates. In some embodiments the fibers momentarily pack into a network until the network or sheet is large enough to interact with the next blade in the assembly, at which time the sheet is pulled into the opposing openings and sheared by the rotating blades or plates. In both cases the water and biomass are mixed under a high shear environment increasing the hydration and enhancing the retained water content of the biomass. Various alternative design configurations are applicable to the rotor and stators, and any specific configuration or orientation of the holes patterns and disk configuration are not intended to limit the innovation. After the biomass passes thru the high shear zone 324 it has been well mixed, hydrated and dispersed and enters the centrifugal pump zone 325 which incorporates a centrifugal impeller 355 to drive the biomass outward toward the inside diameter of the housing 346 and the discharge impeller zone 326. As in the previous embodiments the discharge impeller zone 326 uses sweep bars 336 to collect the hydrated biomass along the housing wall and transfer it to the exit port 304 where the force from the centrifugal pump impeller support transport out of the unit. The exit port 304 is also oriented tangentially to the device body to enhance the discharge of biomass from the device. Any of the alternative configurations for the discharge impeller 336 are applicable to this configuration of the device as previously discussed.

Figure 4:
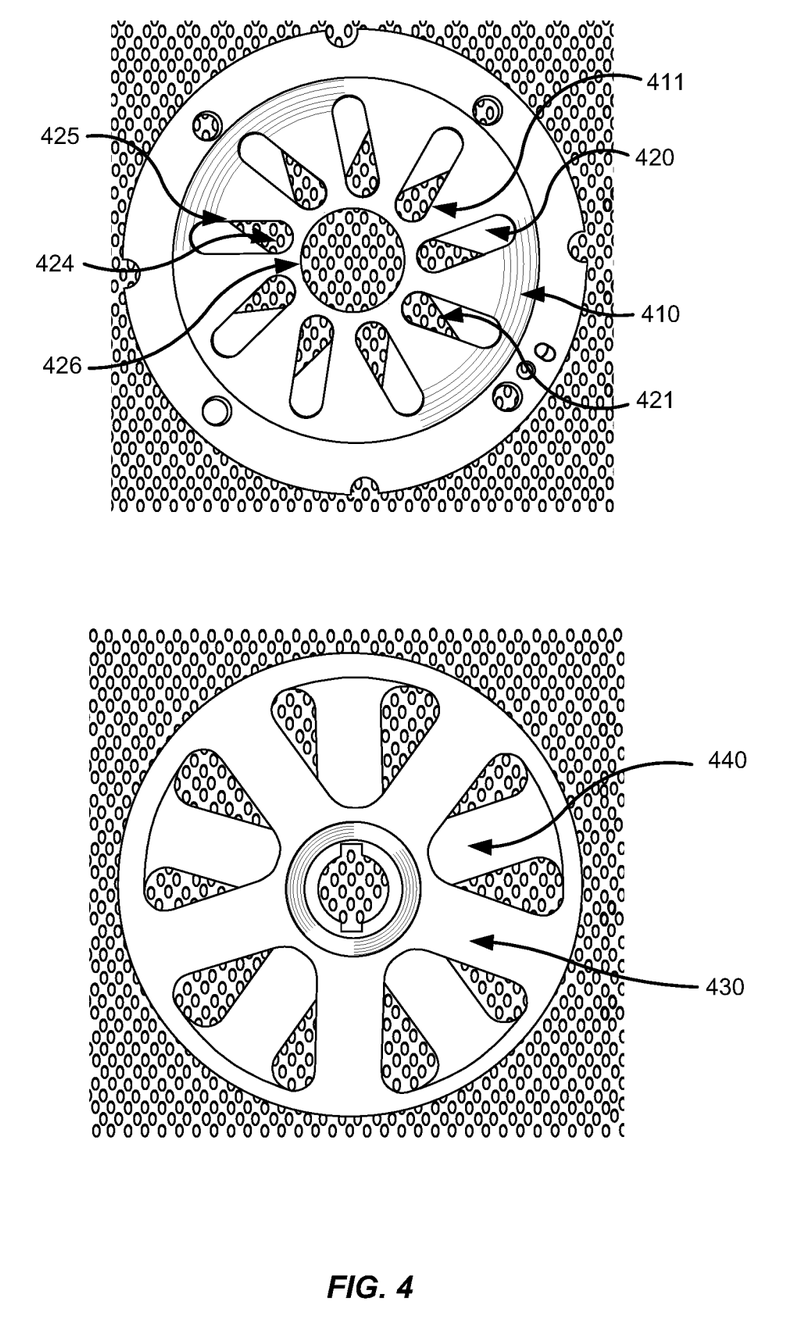
FIG. 4 illustrates an exemplar rotor stator disk configuration.
Figure 5:
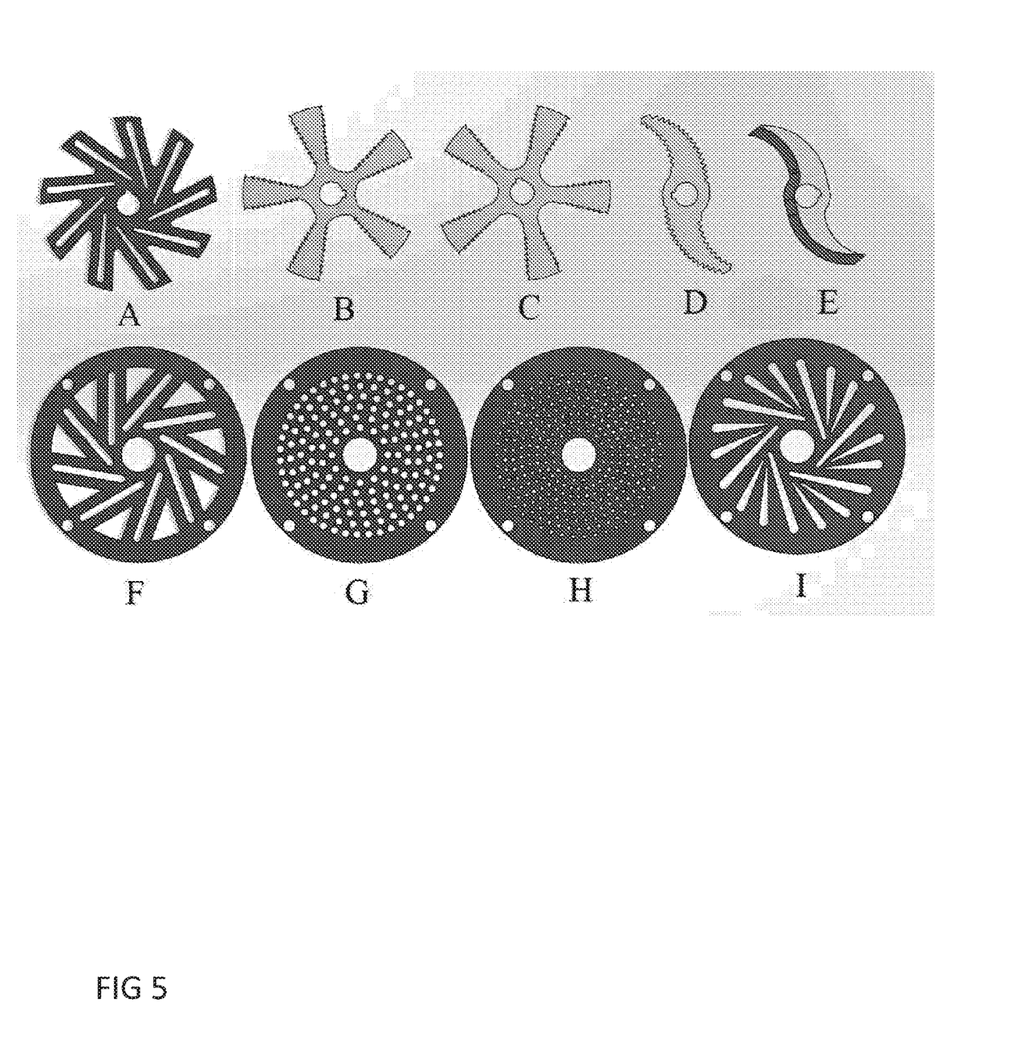
FIG. 5 illustrated several additional exemplar rotor stator disk configurations.

The high shear rotor stator assembly 334 is further illustrated in FIG. 4 and FIG. 5, With respect to FIG. 4 two alternative rotor and stator configurations are illustrated. Stator 410 has been placed above rotor 420 and both rotor and stator have oblong slots or holes with edges 411 in the stator and edges 421 in the rotor. The patterns of opening are positioned such that at any given rotation, open areas 424 exist for biomass to flow thru the opening. In this illustration if the rotor 420 is rotating clockwise the cutting intersection 425 of the rotor and stator will progress radially inward toward the center. The hole 426 is for the drive shaft. An alternative rotor stator pattern is shown stator 430 and rotor 440. Other alternative of the rotor and stator configuration are shown in FIG. 5. In this example the rotors are labelled A, B, C, D and E while the stators are labelled F, G, H, and I. The rotors can be locked to the drive shaft of the device and the stators are assembled and locked to the housing assembly of the device. In some embodiments of the high shear assembly 334 the stators are equipped with circular or rectangular or hexagonal holes such as examples G and H and in some embodiments the holes are more associated with slots such as examples F and I. The assembly 334 can consist of one rotor and one stator or multiple alternating rotor and stators. In some embodiments there are 2 rotors and 2 stators, in some there are 3 rotors and 3 stators, and 4 or more rotor stator combinations. In one embodiment there is one more rotor than stator such that the top and the bottom of the assembly consist of rotating disks. In one embodiment there is one more stator than rotor such that the top and bottom of the stack consist of stationary disks.

In some embodiments of the assembly the design, materials of construction, and spacing of the rotors and stators are such that the replacement cost of the high shear assembly 334 is relatively low so that periodic replacement of the assembly does not contribute significantly to the overall operating cost of the process. The replacement cost for a stack of cutting disk rotor and stators can be approximately $300-500 per assembly. The alternative to this configuration is to use a colloidal mill downstream of the HMD device for the function of particle size reduction. Replacement cost for equivalent capacity wear component in this equipment may be in the range of $20 k to $40 k per year. If the cutting disks required replace 10 times per year, the cost of the replacement components would be less than 25% of the colloidal mill alternative. The embodiment of the MHD with the high shear cutting elements provides lower reoccurring costs on the order of less than 25%, less than 20% or less than 10% of the colloidal mill alternative.

The biomass fibers can be introduced into the device as a relatively long strands of fiber for example as received corn stover and the advantage of the mixing, hydrating, and dispersion device 300 with the high shear cutting assembly 334 is a single step process that reduces the fiber to short pieces and hydrating the fiber and fibril sub structures of the biomass. The feedstock can consist of a mixture of fibers with 10% by weight of the fibers having lengths greater than 2 cm, or greater than 3 cm, or 4 cm or 5 cm or 6 cm or longer. The feedstock can also consist of material that has be preprocessed by dry milling steps (e.g., hammer mills, roller mills, grinders, etc.) such that 90% by weight of the material has a particle size less than 3 mm but still contains a 5 to 20% of the material with particles greater than 1 mm in size. The mechanical shear during the hydration process rips, cuts, and disturbs the fiber structure such that 95% wt of the particles (or greater) are less than 1 mm in size or less than 0.5 mm, or such that 97% of the particles (or greater) are less than 1 mm in size or less than 0.5 mm. The mechanical shear during the hydration process results in producing an exit hydrated biomass with greater than 50%, greater than 55%, or greater than 60% retained moisture. Bulk solids loading is in the controlled ranges of greater than 15%, greater than 20%, greater than 25%, or greater than 30% bulk solids. In addition the device hydrates biomass with the combination of particle size reduction, retained moisture content and bulk solids.

One embodiment of the process is to have a feed hopper deliver biomass fibers to the MHD hardware in which the material is mixed, hydrated (e.g., mixed with water or liquid), and dispersed to create a biomass mixture with a bulk solids level of greater than 15% solids, or greater than 20% solids, or greater than 30% or greater than 40% solids and has a WRV of greater than 2.5 or greater than 3.0 or greater than 3.5. One embodiment of the process is a feed hopper feeding the MHD, which creates a hydrated biomass mixture that with a bulk solids level of greater than 15% solids, or greater than 20% solids, or greater than 30% or greater than 40% solids and has sufficient delivery pressure capability to feed a downstream colloidal mill, which provides high shear particle size reduction capability such that the delivery pressure of the MHD is greater than 30 psig, or greater than 40 psig, or greater than 50 psig in steady state operation or has the capability to achieve greater than 120 psig if deadheaded. One embodiment of the process is to have a feed hopper deliver biomass pellets of bulk density greater than 0.5 kg/lit to a MHD configuration that breaks up the pellets and hydrates the biomass such that the hydrated biomass has a WRV of greater than 2.5, or greater than 3.0 or greater than 3.5 and with a bulk solids level of greater than 15% solids, or greater than 20% solids, or greater than 30% or greater than 40% solids. One embodiment of the process is a MHD configuration containing a high shear zone with alternating stator cutting disks and rotor cutting disks with at least two stators or at least three stators or at least four stators or at least five stators such that feed biomass with a mixture of fiber lengths and greater than 5% of the fibers are longer than 1 inch or longer than 2 inches or longer than 3 inches is mixed, hydrated, and dispersed and exits the MHD with a particle size reduction such that less than 1% of the fiber mass has a length of greater than 0.05 inches or greater than 0.04 inches or greater than 0.03 inches or greater than 0.02 inches and or has a WRV of greater than 2.5 or greater than 3.0 or greater than 3.5 and has a bulk solids level of greater than 15%, or greater than 20%, or greater than 30% or greater than 40%. One embodiment of the process is a feed hopper or biomass conveyor unit delivers biomass fibers to a MHD that delivers hydrated biomass to a colloidal mill, such that the hydrated biomass with a WRV of greater 2.0 or greater than 2.5 or greater than 3.0, can flow to the colloidal mill and has a measurable pressure head of greater than 30 psig, greater than 40 psig, or greater than 50 psig as it exits the MHD, such that no pump is required between the MHD and the colloidal mill.

In one embodiment of the system the mechanical pretreatment (MPT) function for preparing biomass for saccharification consists of two individual pieces of equipment. The first is the MHD device of various configurations, which provides initial mixing, hydration and dispersion of the biomass, and the second is the colloid mill or rotor stator device, which provides the particle size reduction and optimization while producing a homogeneous slurry for downstream processes. In some embodiments the MPT function consists of an integrated device, which incorporates both the elements required for mixing, hydration and dispersion and also includes the rotor stator high shear milling elements as illustrated in FIGS. 3, 4, and 5. In one embodiment the MPT function is places upstream of any thermal pretreatment (TPT) or chemical pretreatment (CPT) or combined chemical/thermal pretreatment (C/TPT). In some embodiments the MPT function can be placed downstream of the TPT, CPT, or C/TPT processes, in some embodiments the biomass is processed by a solids liquid separations (SLS) function and equipment comprising equipment such as a Vincent Press, filter press, vibrating screen separator (e.g., SWECO of Florence, Ky.), centrifuge, wedge wire filter, screen filter, rotary filter, J-Screen (e.g., Johnson Screens of New Brighton, Minn.), and others combination of devices that effectively separate a biomass mixture into a solids stream comprising biomass solids and some liquid and into a liquid stream comprising hulk liquid and dissolved solids and some fine suspended solids. In some embodiments the SLS function is placed downstream of the MPT function to separated residual and/or native sugars or dissolved solids. In some embodiments the SLS function is placed downstream of the TPT, CPT, C/TPT functions to separate by-products or inhibitor from downstream processes such as enzymatic saccharification.

The resulting equipment tandem customization including units tailored for biomass in both MHD and milling unit operations—can be ideally used for the pretreatment of cellulosic biomass substrates in the generation of cellulosic sugars, the key intermediate to either ethanol or other biofuels and biochemicals. Two such substrates of immediate commercial interest are corn stover and sugarcane bagasse, as primary examples. The elements of the device in various embodiments will include a combination of the functional elements outlined in Table 1. For example the device can comprise combination of 1-4-5-7-8-13-14-15-16-18-20 if the biomass feedstock is dry pellets, or can comprise combination of 1-2-3-4-5-9-10-13-14-16-19-20 if the biomass feedstock is dry loose fibers. In another embodiment the device can comprise combination 1-4-5-9-10-14-16-19-20 if the feedstock is dry loose fibers or various lengths and minimal preprocessing.

TABLE 1

List of Optional Elements used in the Assembly of the Device

| Section of device | Element | Location |
| --- | --- | --- |
| Feed Zone | 1. Inlet port | Stator |
| | 2. Biomass scraper prongs | Rotor |
| | 3. Feed auger | Rotor |
| Hydration Zone | 4. Liquid feed port | Stator |
| | 5. Liquid distribution wall or roof | Stator |
| | 6. Feed auger | Rotor |
| | 7. Paddle mixing bars | Rotor |
| High Shear Zone | 8. Paddle mixing bars | Rotor |
| | 9. Rotor cutting disks | Rotor |
| | 10. Stator cutting disks | Stator |
| | 11. Colloid mill rotor assembly | Rotor |
| | 12. Colloid mill stator assembly | Stator |
| Centrifugal Pump Zone | 13. Isolation disk | Stator |
| | 14. Centrifugal pump impeller | Rotor |
| | 15. Stator wall barrier | Stator |
| Discharge Impeller Zone | 16. Sweeping discharge impeller | Rotor |
| | 17. Variable speed drive assembly | Rotor |
| Exit Zone | 18. Exit port | Stator |
| | 19. Tangential exit port | Stator |
| Center Rotating section | 20. Drive shaft for assembling elements | Rotor |

Some preferred embodiments of the device are defined in Table 2 which uses the elements defined in Table 1 and the specific cutting plates as shown in FIGS. 4 and 5. Other combinations are appropriate and these are list as samples of preferred configurations.

TABLE 2

Representative Embodiments of MHD device

| Elements | Configured For |
|---|---|
| 1, 4, 5, 9E, 10I, 9D, 10I, 9C, 10I, 9C, 10G, 9C, 10H, 9C, 14, 16, 19 | Dry Fibrous material up to 6" in length down to 250 micron and above 20% S |
| 1, 9E, 10I, 9D, 10I, 9C, 10I, 9C, 10G, 9C, 10H, 9C, 14, 16, 19 | Wet Fibrous material up to 6" in length down to 250 micron and below 20% S |
| 1, 4, 5, 9E, 10F, 9D, 10F, 9D, 10I, 9D, 10G, 9C, 10H, 9C, 14, 16, 19 | Dry fibrous material up to 9" in length down to 250 micron and above 20% S |
| 1, 3, 4, 5, 7, 7, 7, 7, 13, 14, 16, 17, 19 | Dry powder materials from 0 to 250 microns in size and above 90% S |
| 1, 4, 5, 9E, 10I, 9D, 10G, 9B, 10H, 9B, 8, 8, 14, 16, 19 | Dry fibrous materials up to 850 microns in length down to powder and above 20% S |

In some embodiments where the mixing, hydration, and dispersion functionalities are combined with shear/particle size reduction functionalities in a single MHD unit, and in particular where the thermal pretreatment (TPT) is not downstream of the mechanical pretreatment (MPT), it is possible and advantageous to integrate the intended saccharification or hydrolysis chemical reaction step with the MHD. This can either be done by direct application of the saccharification enzymes (e.g., cellulases, glucanases, xylanases, ligninases, peroxidases, or various combinations of two or more of these enzyme classes) into the high shear or mixing zone(s) of the MHD device, or by introduction of the same enzyme(s) into the pumping and/or discharge section of the MHD, closely downstream of the high shear or mixing zone(s). This configuration thus includes introduction of active saccharification enzymes into one or more of zone(s) 124, 125, and/or 127 (FIG. 1). In addition to process simplification, this embodiment has the benefit of increased effectiveness (conversion efficiency and/or speed) of these enzymes in the saccharification or hydrolysis step, resulting from the intimate contact between enzymes and reactive substrate in the high-solids, small-particle size, homogenous and hydrated state of the substrate slurry found in or immediately after the high-shear zone of the MHD in this configuration.

EXAMPLES

Example 1

An MHD-20 manufactured by IKA Works, USA (Wilmington, N.C.) was customized via the inclusion of the inlet sheer cutting zones and the t high-solids discharge impeller. This unit was deployed in tandem with the Cellunator™ by Edeniq, Inc. (Visalia, Calif.), specifically the IKA MK2000/20 unit, for the purpose of tandem processing of corn stover biomass.

The stover had been initially preprocessed to an approximate upper particle size of 6" prior to this treatment. The material was roughly 95% S by weight.

The material was processed through the tandem MHD-Cellunator train continuously at approximately 15 GPM, and a solids loading of 18% S. From here, the propensity for this material to be used effectively in saccharification processing was independently verified in laboratory testing.

Example 2

An MHD-20 manufactured by IKA Works, USA (Wilmington, N.C.) was customized via the inclusion of the inlet sheer cutting zones and the high-solids discharge impeller. This unit was deployed in tandem with the Cellunator™ by Edeniq, Inc. (Visalia, Calif.), specifically the IKA MK-20 unit, for the purpose of tandem processing of sugarcane bagasse biomass.

The bagasse had been initially preprocessed to an approximate upper particle size of 1.5 mm prior to this treatment, with no upstream thermal treatment processing.

The material was processed through the tandem MHD-Cellunator train continuously at approximately 10 GPM, and a solids loading of 20%. From here, the material was subjected to laboratory thermal pretreatment, and the subsequent propensity for this material to be used effectively in saccharification processing was independently verified in laboratory testing.

Example 3

Figure 6:
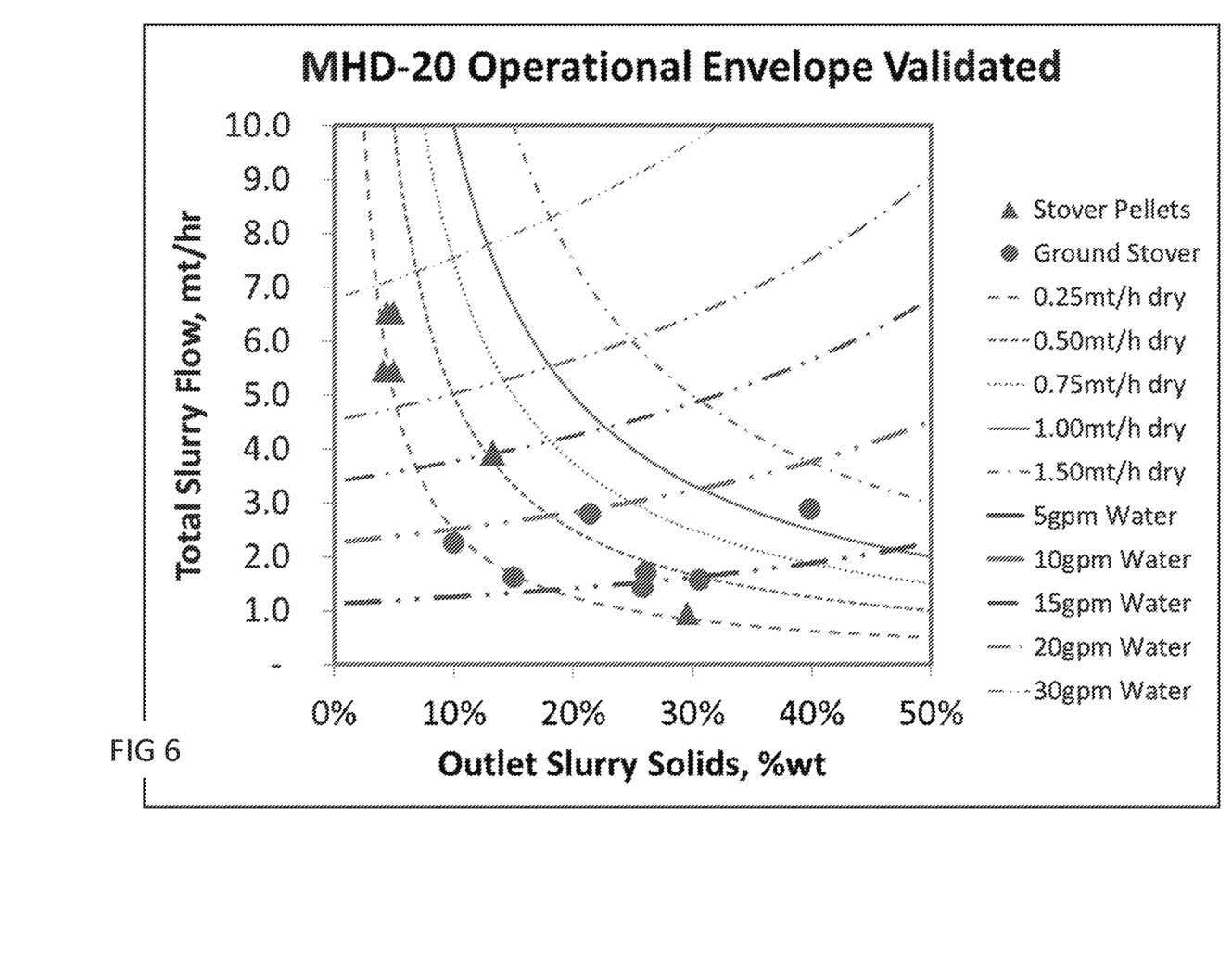
FIG. 6 illustrates operational mapping of a pilot scale version of the inventive device indicating operation of both stover pellets and ground stover.

A configuration of the MHD which incorporated the high shear paddle zone feeding the centrifugal pumping ring, and the sweeping cross bars was operated on both corn stover pellets and loose fiber stover. The processing capabilities of this small scale device (i.e., IKA MHD-20) was partially mapped as a function of total mass flow rate and resulting biomass solids fraction as illustrated in FIG. 6. Both pellets and loose fibers were successfully used to produce homogeneous, viable slurry for downstream processing. When processing pellets the maximum slurry solids validated was approximately 30%, and while processing loose fibers a slurry of approximately 40% solids was achieved. Total mass flow rates as high as 6.5 mt/h was processed using pellets and almost 3 mt/h on loose fibers. The maximum solids feed rate exceeded 1.1 mt/h dry feedstock. These experiments validated a wide operation envelope for the device as illustrated in FIG. 6.

Example 4

Figure 7:
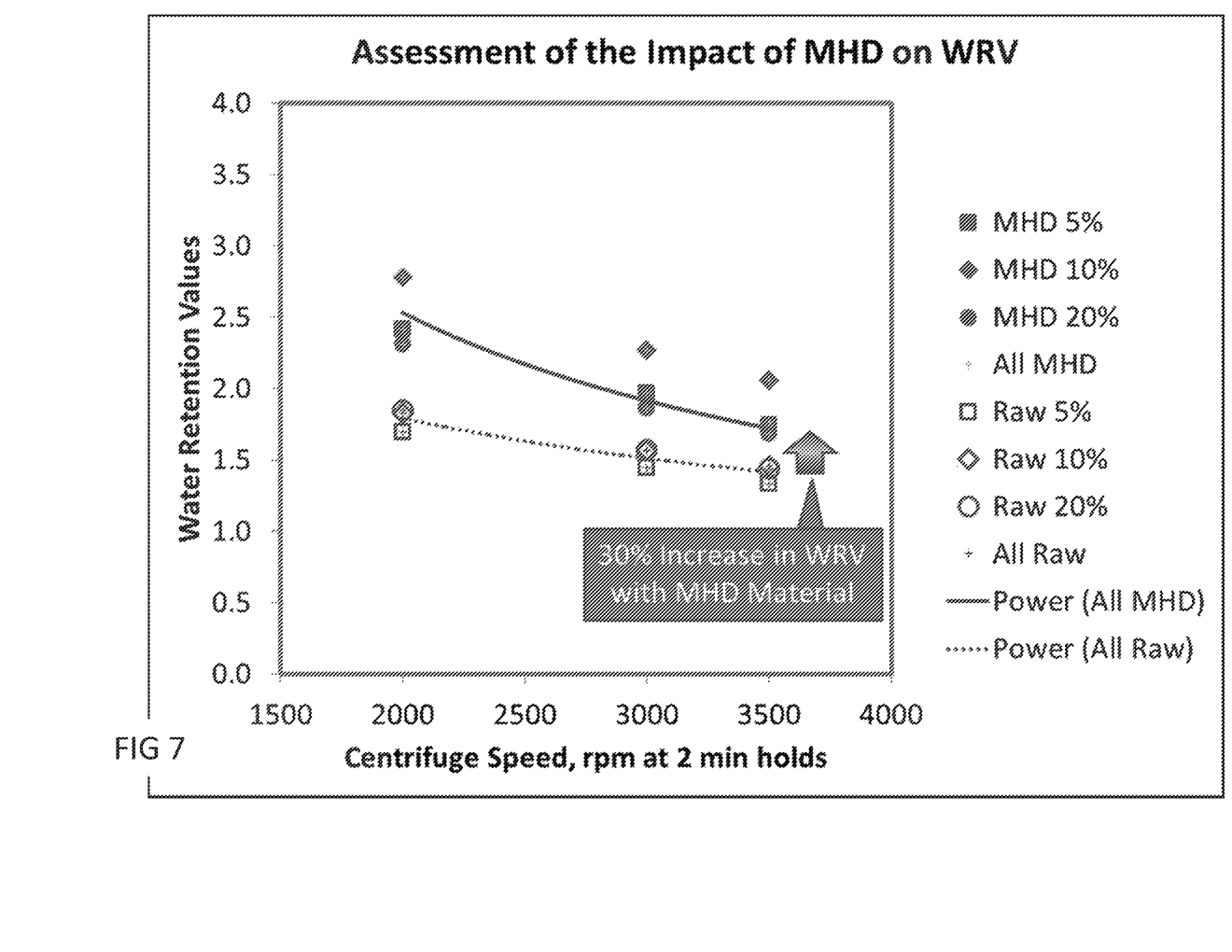
FIG. 7 illustrates the increase in water retention value by comparison of raw material and material treated by the inventive device.

In another example as illustrated in FIG. 7 biomass hydration was compared for bagasse that what hydrated by either a soaking method over 48 hours or processing by the device (i.e. IKA MHD2000/20) The unit was configured as [1, 2, 3, 4, 5, 6, 7, 7, 7, 7, 13, 14, 16, 18, 20], in which the sequence of numbers refer to the combination of functional elements outlined in Table 1 and Table 2, and fed with biomass. The "raw samples" were loose fibers of bagasse biomass that was soaked and stirred in water for 48 hours at ambient temperature ensure they were hydrated, pressed and remixed with water to achieve an initial bulk solids level before measurement of the water retention value. The same loose fibers of bagasse biomass were processed by the device in various lots, "MHD samples", to achieve target solids levels in a single pass through the device. The sets of samples were then tested to measure the water retention value using a lab centrifuge. The 50 ml centrifuge tubes were configured to hold the biomass half way up the tube and allow collection of the removed water. About 10 gm of material was used in each test and two samples were averaged to represent the data set. The protocol allowed the sample to be spun at a fixed speed for 2 minutes at which point the removed liquid was weighed prior or to re-spinning it at a higher centrifugal speed. After the final spin the material was dried to determine the retained solids mass for calculating the water retention value. As indicated in FIG. 7, the MHD sample maintained higher water retention values than the soaked samples and demonstrated a 30% lift in WRV.

Example 5

Figure 8:
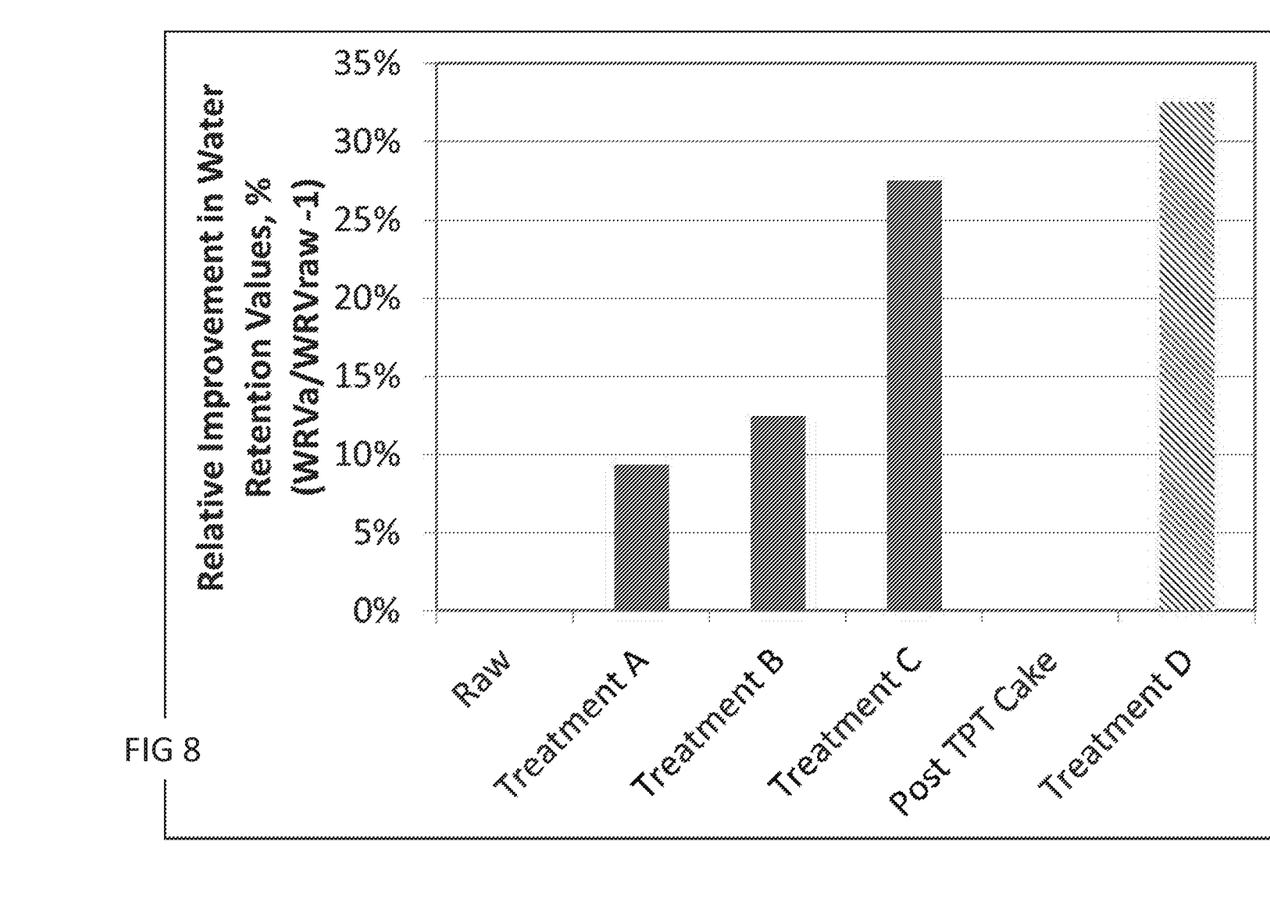
FIG. 8 illustrates the relative improvement in water retention values for various treatments.
Figure 9:
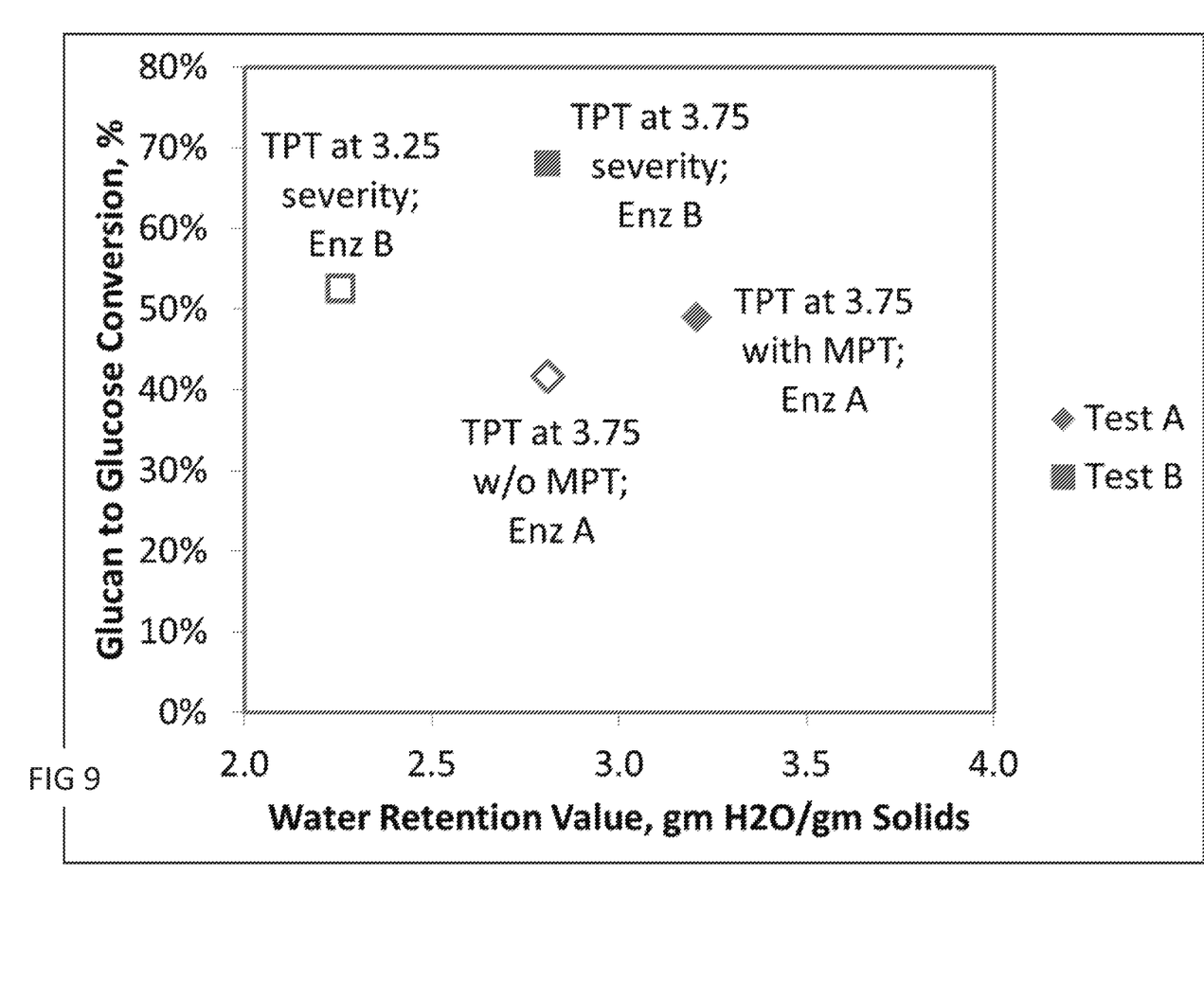
FIG. 9 illustrates the glucan to glucose conversion of various treatments vs the water retention value of the mechanically pretreated biomass.

Another example of the effectiveness of the MHD device and MPT function in hydrating biomass is shown in FIG. 8. In this test the water retention values protocol was modified to assess only the WRV after a single centrifuge separation step at 900×g for 30 minutes and a modified protocol to increase the reliability of the testing. In this experiment five biomass samples were tested, including Raw (i.e., water soaked biomass), Treatment A (i.e. processed by the MHD), Treatment B (i.e., processed by the MHD and colloid mill integrated system), Treatment C (i.e., TPT biomass only), and Treatment D (i.e., TPT biomass that was processed by the MHD and colloid mill post TPT). As clearly indicated the WRY of treatments A, B, and C (i.e., samples prior to TPT) was greater than the raw material, and both the MHD and combined MHD and colloid mill provided enhanced WRV in comparison to the Raw material. An alternative strategy would be to expose the biomass to TPT conditions prior to mechanical pretreatment and the impacts are illustrated in the comparison of Treatment D to post TPT Cake without mechanical treatment. Treatment D illustrates over 30% enhancement in the WRV of the biomass in comparison to the non-mechanically pretreated sample Post TPT cake. Enzymatic conversion is a complex process impacted by enzyme cocktail, dosing strategies, and fiber exposure, while WRY are impacted greatly by particle size in addition to the degree of hydration of the desired intra-fiber water. To assess if the observed increases in WRV correlate with improved saccharification, these materials were saccharified with enzymes to process the glucan and other structural carbohydrates into glucose and xylose sugar monomers. The results for glucan to glucose conversion are illustrated in FIG. 9, which plots the percent glucan to glucose conversion as a function of water retention value for each treatment. Two individual tests are shown—Test A (i.e., diamonds) and Test B (i.e., squares)—to reflect the change in conversion with the change in WRV resulting from (A) mechanical treatment after TPT and from (B) two different TPT conditions. Test A represents TPT biomass that has been additionally treated with a solid liquid separation step and the resulting solids exposed to 48 hours of enzymatic saccharification using baseline dosing of cellulase enzyme A. The open diamond data point is the material with TPT only and the solid diamond data point represents the same material but processed by both solid liquid separation and followed by mechanical processes using the MHD followed by the colloid mill. In this example both increasing WRV and glucan conversion were observed. Test B represents TPT biomass at two different severity factors (i.e., SF of 3.25 open data point and 3.75 solid data point) after saccharification for 24 hr with high dosing of cellulase enzyme B. In this example, the impact of the higher severity TPT also increased both the WRV and the conversion performance.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed:

1. A device for mixing, homogenizing, dispersing, and processing materials, comprising the following components: a. One or more stages of shear cutting elements configured to initially process incoming solids by shear cutting and dispersion prior to or in tandem with water introduction; wherein the one or more stages of shear cutting elements comprises a series of alternating rotor and stator plates; a series of two or more impeller stages positioned in between the shear cutting stages and a discharge impeller stage to enhance mixing and homogenization; c. a pumping ring to direct material flow from an outlet of the discharge impeller stage to a discharge port, wherein the discharge port is configured tangentially to the device's diameter to enhance the delivery pressure of the hydrated biomass.

2. The device of claim 1, further comprising a downstream milling device configured to reduce particle sizes and further homogenize the materials to a pretreated state suitable for downstream enzymatic hydrolysis processing.

3. The device of claim 2, wherein the downstream milling device is a colloidal mill, and the material processed is corn stover or sugarcane bagasse.

4. The device of claim 2, wherein the mixing, homogenizing, dispersing, and processing are accomplished in a hybrid device constructed in a single housing.

5. A device or tandem device(s) for mixing, homogenizing, dispersing, milling and processing of biomass materials, derived from corn stover or sugarcane bagasse, for generating a homogenous, hydrated slurry of biomass solids comprising >20% (by weight) solid material that is readily pumpable and transportable to downstream chemical processing and/or biochemical processing unit operations, comprising the following components:
a. One or more stages of shear cutting elements to initially process incoming solids by shear cutting and dispersion prior to or in tandem with water introduction, wherein the shear cutting elements comprise a series of alternating rotor and stator plates; and wherein the rotor and stator plates have oblong slots or holes; b. a series of two or more impeller stages positioned between the shear cutting stages and a discharge impeller stage to enhance mixing and homogenization; c. a pumping ring to direct slurry flow from an outlet of the discharge impeller to a discharge port; d. one or more colloidal mills or colloidal mill stages that reduces particle size and further enhances slurry phase dispersion; thereby generating a slurry capable of saccharification efficiencies of >70% in processing times of <24 hours.

6. A device or tandem device(s) of claim 5, wherein saccharification enzymes are added into one or more of the shear zone, pumping zone, discharge impeller outlet, or discharge port of the device(s).

7. A device or tandem device(s) of claim 6, wherein the saccharification enzymes introduced directly into one or more of the shear zone, pumping zone, discharge impeller outlet or discharge port of the device(s) are comprised of one or more of the enzyme classes of cellulases, glucanases, xylanases, ligninases, or peroxidases.

8. The device of claim 1, further comprising an isolation disk positioned between the shear cutting stages and the two or more impeller stages.

9. The device of claim 5, wherein the stator comprises (i) circular, rectangular or hexagonal holes, or (ii) slots.

10. The device of claim 5, wherein the discharge port is configured tangentially to the device's diameter to enhance the delivery pressure of the hydrated biomass.

\* \* \* \* \*